(12) United States Patent
Anan et al.

(10) Patent No.: US 9,601,308 B2
(45) Date of Patent: Mar. 21, 2017

(54) SPECTROSCOPIC ELEMENT AND CHARGED PARTICLE BEAM DEVICE USING THE SAME

(71) Applicant: Hitachi, Ltd., Chiyoda-ku, Tokyo (JP)

(72) Inventors: Yoshihiro Anan, Tokyo (JP); Masanari Koguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/439,993

(22) PCT Filed: Oct. 31, 2012

(86) PCT No.: PCT/JP2012/078092
§ 371 (c)(1),
(2) Date: Apr. 30, 2015

(87) PCT Pub. No.: WO2014/068689
PCT Pub. Date: May 8, 2014

(65) Prior Publication Data
US 2015/0318144 A1    Nov. 5, 2015

(51) Int. Cl.
*G01T 1/20*   (2006.01)
*H01J 37/244*   (2006.01)
*G01N 23/225*   (2006.01)
*H01J 37/28*   (2006.01)
*G21K 1/06*   (2006.01)
*H01J 37/252*   (2006.01)

(52) U.S. Cl.
CPC ........ *H01J 37/244* (2013.01); *G01N 23/2252* (2013.01); *G21K 1/067* (2013.01); *H01J 37/28* (2013.01); *G21K 2201/064* (2013.01); *H01J 37/252* (2013.01); *H01J 2237/2442* (2013.01); *H01J 2237/2445* (2013.01)

(58) Field of Classification Search
CPC ......... G01T 1/20; G01T 1/202; G01T 1/2023; G01T 1/2002; G21K 4/00
See application file for complete search history.

(56) References Cited

U.S. PATENT DOCUMENTS 7,656,170 B2 *   2/2010   Pinto ...................... H01L 22/34
                                                          324/501
2002/0158200 A1   10/2002   Terauchi
(Continued)

FOREIGN PATENT DOCUMENTS

JP   2002-329473 A   11/2002
JP   2004-294168 A   10/2004

*Primary Examiner* — David Porta
*Assistant Examiner* — Mamadou Faye
(74) *Attorney, Agent, or Firm* — Miles & Stockbridge P.C.

(57) ABSTRACT

To analyze an element to be evaluated with high sensitivity and high accuracy in a short period of time, in an electron beam analyzer including a wavelength dispersive X-ray analyzer in an electron microscope. The electron beam analyzer has one diffraction grating in which a plurality of patterns having maximum X-ray reflectance with respect to the respective X-rays are formed. It simultaneously detects an X-ray as an energy reference and an X-ray spectrum to be evaluated. The positional displacement of X-ray energy due to the installation/replacement of the diffraction grating is corrected using the X-ray spectrum as the energy reference, thereby enabling to perform an analysis with high sensitivity and high accuracy in a short period of time.

11 Claims, 6 Drawing Sheets

(56) References Cited

U.S. PATENT DOCUMENTS

| | | | | |
|---|---|---|---|---|
| 2009/0052620 A1* | 2/2009 | Takakura | ............ | G01N 23/2252 |
| | | | | 378/45 |
| 2009/0146309 A1* | 6/2009 | Kudo | ................ | H01L 21/76829 |
| | | | | 257/768 |
| 2012/0275870 A1* | 11/2012 | Paseuth | ................. | C23C 30/005 |
| | | | | 407/119 |
| 2012/0287257 A1* | 11/2012 | Chino | ..................... | H01J 37/22 |
| | | | | 348/80 |
| 2014/0295070 A1* | 10/2014 | Tsuru | ....................... | C25D 5/10 |
| | | | | 427/123 |
| 2015/0076346 A1* | 3/2015 | Weiss | ..................... | H01J 37/26 |
| | | | | 250/307 |

* cited by examiner

ENERGY DEPENDENCE OF X-RAY REFLECTANCE OF DIFFRACTION GRATING

BLAZE ANGLE $\theta 1_B$

BLAZE ANGLE $\theta 2_B$

ENERGY DEPENDENCE OF X-RAY REFLECTANCE OF
BLAZED TYPE DIFFRACTION GRATING

SPECTROSCOPIC ELEMENT AND CHARGED PARTICLE BEAM DEVICE USING THE SAME

TECHNICAL FIELD

The present invention relates to a charged particle beam device using an X-ray spectroscopic element in a micro area, using an electron beam, and an analytical method, and, more particularly, to an electron beam analyzer, in which a scanning electron microscope (SEM) and a scanning transmission electron microscope (STEM) are installed in an analyzer and which analyzes those elements included in a sample at a high resolution and with high sensitivity and high accuracy, and its analytical method.

BACKGROUND ART

As an X-ray analytical technique in a region of nanometer order, known techniques are a SEM-EDX (STEM-EDX) or a SEM-WDX (STEM-WDX), for scanning an extremely fine electron probe on a sample and dispersing an X-ray generated from an irradiated local region with an electron beam. (EDX; Energy Dispersive X-ray Spectroscopy, WDX; Wavelength Dispersive X-ray Spectroscopy). The SEM-EDX (STEM-EDX) or the SEM-WDX (STEM-WDX) is a device in which an energy dispersive X-ray spectrometer (EDX) is installed in a SEM (STEM) or a wavelength dispersive X-ray spectroscopy is installed therein.

The WDX spectroscopy is a spectroscopy, which drives a diffraction grating as a dispersive crystal and uses a Bragg diffraction equation ($2d\sin\theta = n\lambda$). "d" represents the space of a lattice plane of the diffraction grating, "$\theta$" represents an incidence angle at which an X-ray enter the lattice plane, "n" represents a diffraction order, and "$\lambda$" represents the wavelength of the X-ray. The WDX spectroscopy can perform an analysis with high sensitivity and with high accuracy, because overlapping of the X-ray spectrums can be eliminated, and because the energy resolution is higher (one or more than one digit larger) than an energy resolution 120 eV of the EDX spectroscopy, and the energy resolution is in a rang between several eV to tens of eV. That is, the energy resolution is larger than the energy resolution 120 eV of the EDX spectroscopy.

Generally, there are two types of WDX spectroscopy. As illustrated in FIG. 1, one type of WDX spectroscopy disperses and detects an X-ray, while rotating a planer shaped diffraction grating 16 with a multilayer film and driving an X-ray detector 18. To realize parallel entering of the X-ray toward the planer shaped diffraction grating 16, and to increase the yield of an X-ray 3 generated from the sample 15, an X-ray condensing lens 19 is provided between the sample 15 and the diffraction grating 16 (for example, Patent literature 1). To realize parallel entering of the X-ray 3 toward the diffraction grating 16, slits may sometimes be provided between the sample 15 and the diffraction grating 16.

As illustrated in FIG. 2, in the other type of spectroscopy, a curved-type (called as Johann or Johansson-type) diffraction grating 20 and the detector 18 are provided. In addition, the X-ray is dispersed and detected, while the curved-type diffraction grating 20 and the detector 18 are driven on a Rowland circle 21. In Patent literature 2, to have a compact X-ray detection system, an irregularly spaced diffraction grating is used for a dispersive crystal, and an X-ray is caused to obliquely enter the irregularly spaced diffraction grating. Then, a plurality of diffracted rays of light dispersed by the irregularly spaced diffraction grating are simultaneously detected by a CCD detector. To correspond to a high energy X-ray from a low energy one, a plurality of diffraction gratings are prepared, and there is provided a mechanical mechanism for exchanging and replacing/installing the diffraction grating, to select/install the diffraction gratings in accordance with X-ray energy of a target to be analyzed. As described above, the WDX device using the irregularly spaced diffraction grating and a position detector (CCD) acquires an X-ray spectrum as a reference of an energy position and an X-ray spectrum of a target to be evaluated. An energy value of the X-ray spectrum of the target to be evaluated is obtained based on a relative amount of X-ray spectrum energy position as a reference.

CITATION LIST

Patent Literature

Patent Literature 1: Japanese Unexamined Patent Application Publication NO. 2004-294168
Patent Literature 2: Japanese Unexamined Patent Application Publication No. 2002-329473

SUMMARY OF INVENTION

Technical Problem

FIG. 4 is a diagram illustrating the examinations made by the present inventors prior to the inventions, for explaining the object of the present application. As illustrated, X-ray reflectance of the diffraction grating has energy dependence of the X-ray. Thus, in the use of a diffraction grating 22 with a form for attaining the highest X-ray intensity of X-ray energy E2 of the target to be evaluated, the X-ray intensity of X-ray energy E1 as a reference will remarkably decrease.

Therefore, the energy of the X-ray spectrum of the target to be evaluated will not sufficiently be corrected, resulting in lowering the measurement accuracy, because of the low intensity of the X-ray spectrum as a position reference of energy. It may be considered to use a diffraction grating with a shape for realizing the same reflectance between the target X-ray, to be evaluated, of the X-ray energy E2 and the X-ray as an energy position reference of the X-ray energy E1. However, the measurement sensitivity decreases, because the intensity of the X-ray spectrum of the target to be evaluated decreases, while the intensity of the X-ray spectrum as a reference increases.

In Patent literature 2, positional displacement of the diffraction grating occurs at the replacement/installation, if mechanical replacement/installation is made to prepare the irregularly spaced diffraction grating whose spectrum intensities of the reference/measurement are detected as a high value. Thus, the focus position of the X-ray dispersed by the diffraction grating is displaced and detected by a CCD detector. The positional displacement of the diffraction grating occurs by the replacement of the diffraction grating, thus requiring the position/rotation adjustment and resulting in time loss.

The CCD detection position in the vertical direction to the plane of the diffraction grating corresponds to the energy of the X-ray. Positional displacement of the energy of the X-ray is resulted from the positional displacement of the X-ray detection by the CCD, in accordance with the positional displacement of the diffraction grating. As a result, it may deteriorate precisions of the elemental analysis and the analysis of the electronic state, corresponding to the energy position of the X-ray.

Solution to Problem

The representative inventions, as will be disclosed in the present application, will briefly be described as follows.

A spectroscopic element of the present invention is characterized to include a first pattern for dispersing an applied X-ray as a spectrum and a second pattern for generating spectrum different from that of the first pattern, for the applied X-ray.

The charged particle beam device of the present invention has an irradiation optical system for irradiating a charged particle beam toward a sample and an X-ray detection system for detecting an X-ray generated from the sample. The X-ray detection system has a spectroscopic element, which has a first pattern for dispersing the X-ray as a spectrum and a second pattern for generating a spectrum, different from that of the first pattern, for the X-ray.

Advantageous Effects of Invention

According to the brief descriptions of the present invention, it is possible to realize a high sensitive analysis.

DESCRIPTION OF EMBODIMENTS

Figure 1:
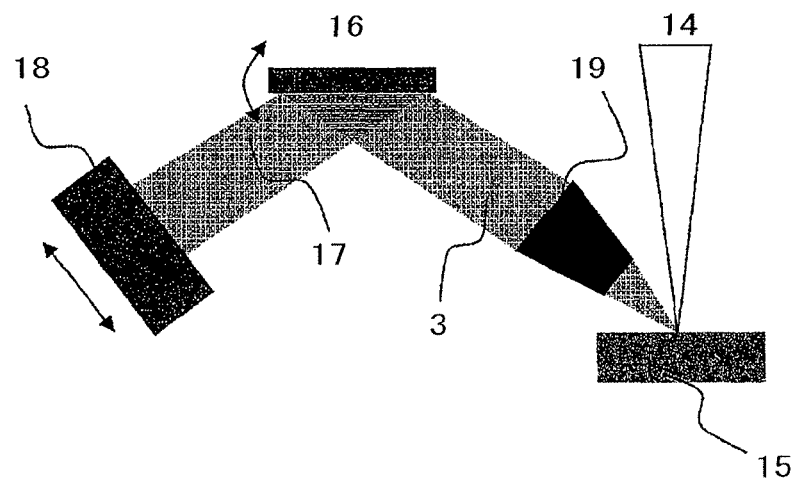
FIG. 1 is a side view illustrating a wavelength dispersive X-ray analyzer (WDX) using a conventional planer shaped diffraction grating with a multilayer film.
Figure 2:
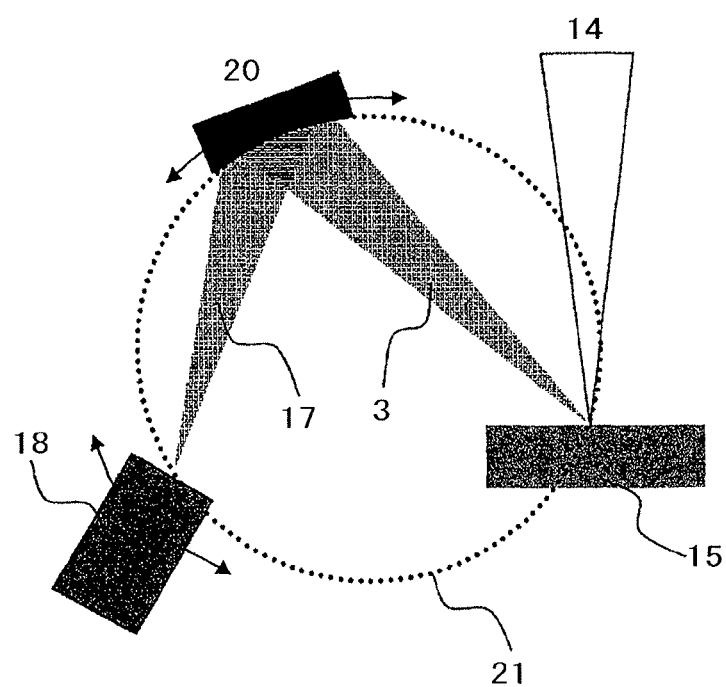
FIG. 2 is a side view illustrating a wavelength dispersive X-ray analyzer (WDX) using a conventional diffraction grating with a curved form.

A charged particle beam device according to the present invention has a configuration which includes an electron optical system irradiating an electron beam onto a sample to be inspected, means for detecting secondary electrons generated form the irradiated part with an electron beam or detecting electrons transmitting through or scattered in the sample to be inspected, an X-ray spectroscopic element (hereinafter referred to as a diffraction grating) dispersing an X-ray generated from the irradiated part with the electron beam, and a position detector detecting the X-ray dispersed by the diffraction grating. In this configuration, as the diffraction grating, one diffraction grating has a first and second of patterns (plural) for generating different spectrums for an X-ray entering the diffraction grating. The first and second patters are characterized to be formed based on the intensities of the X-ray reflectance as a reference of the energy position and the X-ray reflectance of a target to be measured.

In the first pattern, the X-ray as the reference of the energy position is diffracted at maximum reflectance. In the second pattern, the X-ray of the target to be evaluated is diffracted at maximum reflectance. It is possible to simultaneously detect the X-ray intensity distributions with high X-ray intensity, using the position detector. This attains an X-ray with high X-ray intensity and corrects displacement of the X-ray energy position which has occurred due to mechanical replacement/installation of the diffraction grating.

This results in increasing the sensitivity for the X-ray of the target to be evaluated and the accuracy of the X-ray energy position. Thus, it is possible to evaluate the sensitivity of an elemental analysis in the sample and to evaluate an analysis of an electronic state with high accuracy.

Conventionally, to increase the accuracy of the X-ray energy position, it has taken a lot of time to adjust the position of the diffraction grating. However, according to this invention, because there is no need to adjust the position of the diffraction grating with high accuracy, it is possible to reduce a time loss and to perform the elemental analysis with high accuracy in a short period of time.

Descriptions will now specifically be made to preferred embodiments of the present invention based on the drawings. In the entire drawings for explaining the embodiments, the same reference numerals are generally given to the same components, and the same components will not repeatedly be described again. The aforementioned and other objects and new features of the present invention will be apparent from the descriptions of the present specification and attached drawings.

(Embodiment 1)

Figure 5:
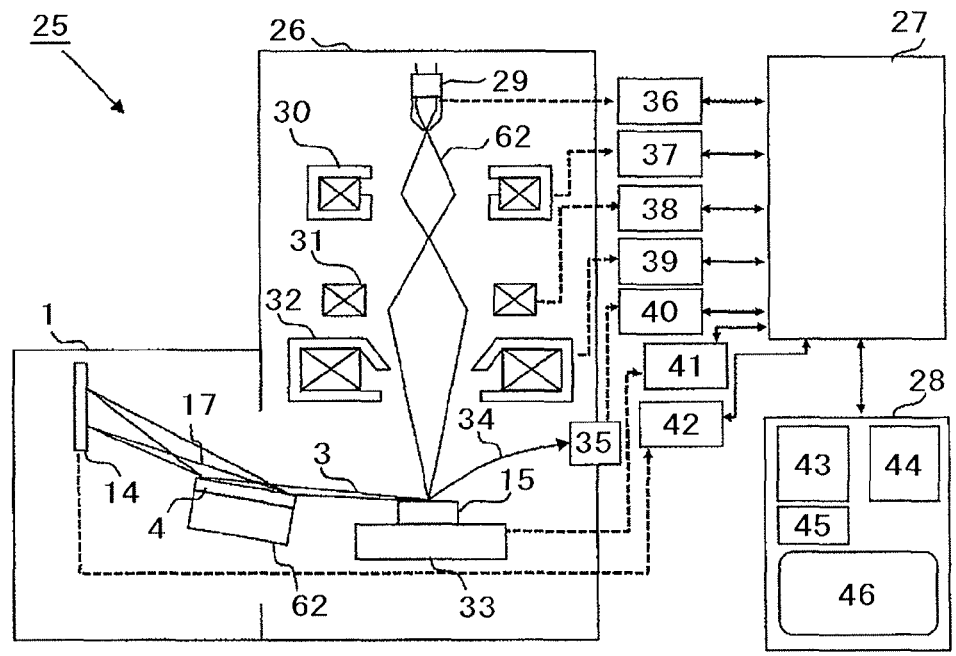
FIG. 5 is a side view for explaining an electron beam analyzer as an embodiment of the present invention.

FIG. 5 is a schematic diagram illustrating a configuration example of an electron beam analyzer 25 in an embodiment 1. The electron beam analyzer 25 illustrated in FIG. 5 is formed of a scanning electron microscope device 26, an X-ray analyzer 1, a control system 27, and an operation unit 28. The scanning electron microscope device 26 is formed of an electron gun 29, a condenser lens 30, an electron beam deflector 31, an objective lens 32, a sample stage 33, and a secondary electron detector 35. The X-ray analyzer 1 is formed of a diffraction grating 4 and an X-ray position detector 14.

The control system 27 is formed of an electron gun control unit 36, a condenser lens control unit 37, an electron beam deflector control unit 38, an objective lens control unit 39, a secondary electron detection system circuit control unit 40, a stage control unit 41, and an X-ray detection system circuit control unit 42. The operation unit 28 is formed of an image display unit 43, an X-ray image and X-ray spectrum display unit 44, a storage unit 45 storing stage positions, secondary electron images, X-ray images, and spectrums, and an operation screen 46. As illustrated, the X-ray analyzer 1 and the scanning electron microscope device 26 may be incorporated as one device. Needless to say, however, they may be separated, as long as the functions of the X-ray analyzer 1 are realized.

A primary electron beam 61 generated from the electron gun unit 29 is narrowed by the objective lens 32 and irradiated on a sample 15. At the irradiation onto the sample 15, the scanning speed and the scanning region are controlled by the deflector 31. Secondary electrons 34 generated from the irradiated part with the primary electron beam 61 are detected by the secondary electron detector 35.

Figure 6:
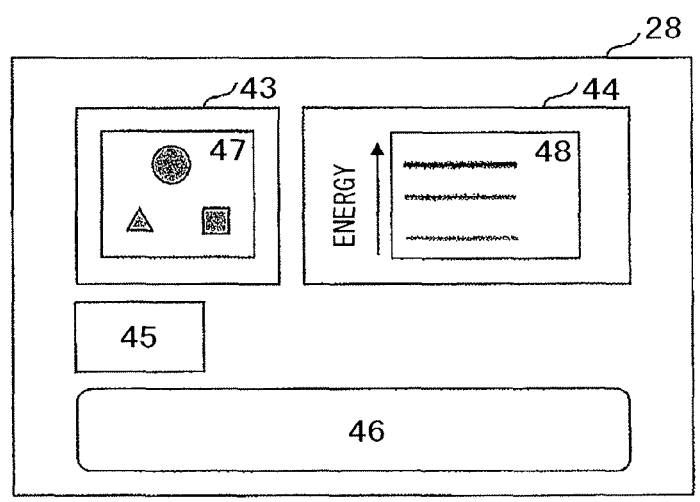
FIG. 6 is a diagram for explaining an electron beam analyzer as an embodiment of the present invention.

As illustrated in FIG. 6, a secondary electron signal detected by the secondary electron detector 35 is synchronized with a scanning signal of the primary electron beam 61 and output, thereby displaying a secondary electron image 47 of the sample 15 on the image display unit 43. In the X-ray analyzer 1, an X-ray 3 generated from the irradiated part of the sample 15 with the primary electron beam 61 is made to enter the diffraction grating 4 and dispersed. An X-ray 17 dispersed by the diffraction grating 4 is detected by the X-ray position detector 14. The position/angle of the diffraction grating 4 are adjusted by a diffraction grating position/rotation adjustment mechanism 62. As illustrated in FIG. 6, the detected X-ray is to display an X-ray image 48 on the X-ray image and spectrum display unit 44.

Figure 7:
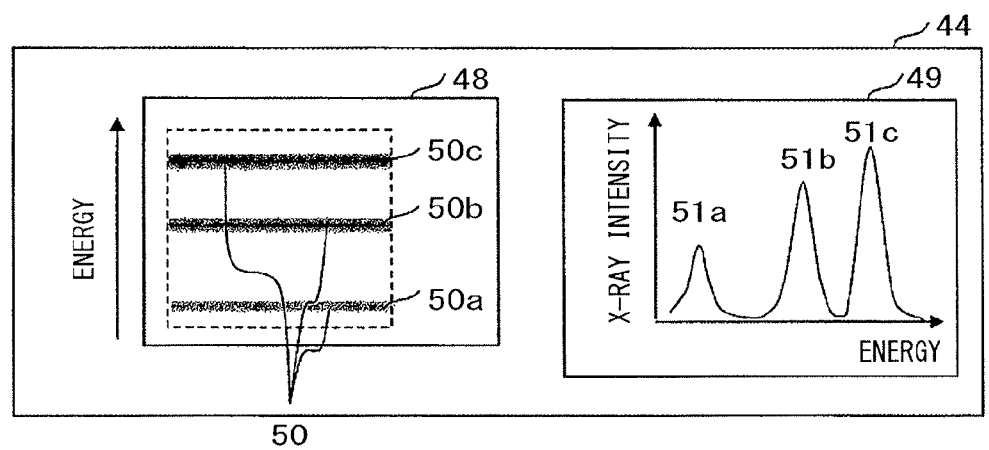
FIG. 7 is a diagram for explaining an electron beam analyzer as an embodiment of the present invention.

In the X-ray image 48 illustrated in FIG. 7, the X-ray intensities are integrated or averaged in a direction perpendicular to the X-ray energy axis. An X-ray spectrum 49 is capably displayed on the X-ray image or X-ray spectrum display unit 44. In the X-ray spectrum 49, the X-ray energy is plotted on the horizontal axis, while the integrated value and the average value of the X-ray intensities are plotted on the vertical axis. X-rays of X-ray intensity distributions 50a, 50b, and 50c in the X-ray image 48 respectively correspond to 51a, 51b, and 51c in the X-ray spectrum 49. Like the case of obtaining the secondary electron image 47, the X-ray intensity (for example, 50a) included in X-ray intensity distributions 50 detected by the X-ray position detector 14 is selected, and an X-ray signal (50a) is synchronized with the scanning signal of the primary electron beam 61 and output. This enables to display an element map image 52 on the image display unit 43. The image output of an image display unit 43a is changed, thereby enabling to display the secondary electron image 47 or the element map image 52.

Figure 8:
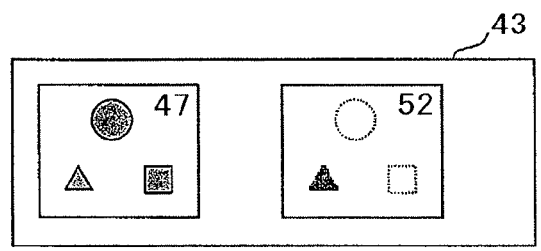
FIG. 8 is a diagram for explaining an electron beam analyzer as an embodiment of the present invention.

As illustrated in FIG. 8, two screens are provided in the image display unit 43, and thus can simultaneously display the secondary electron image 47 and the element map image 52.

Figure 3:
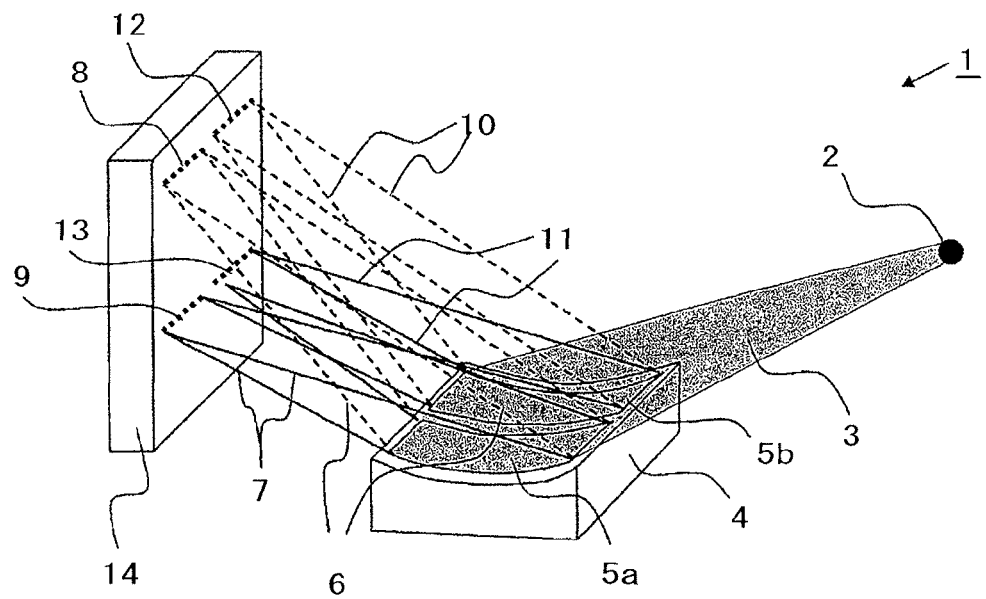
FIG. 3 is a perspective view for explaining an X-ray detection system component part of an electron beam analyzer as an embodiment of the present invention.
Figure 4:
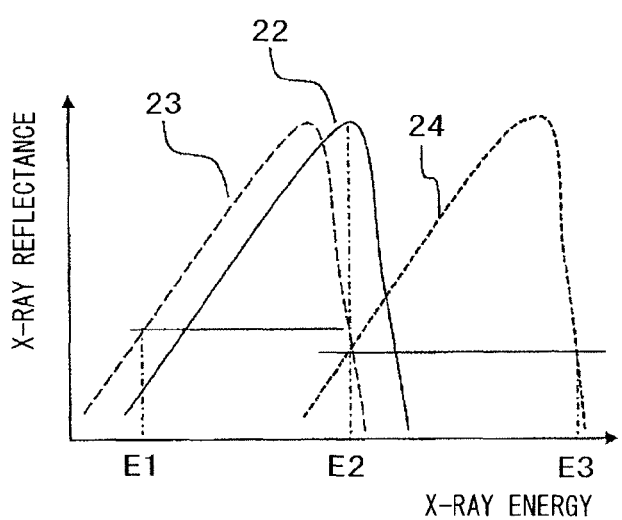
FIG. 4 is a diagram illustrating the energy dependence of the X-ray reflectance of a diffraction grating, showing the object of the present invention.

As illustrated in FIG. 3, in the present X-ray analyzer 1, in the diffraction grating 4 of the X-ray analyzer 1, one diffraction grating is characterized to be formed with a first pattern 5a and a second pattern 5b for generating different spectrums for the X-ray 3 entering the diffraction grating. An X-ray 6 and an X-ray 7 dispersed by the first pattern 5a are focused on the X-ray position detector 14, resulting in an X-ray intensity distribution 8 and an X-ray intensity distribution 9 with a linear form. Like the dispersion by the first pattern 5a, an X-ray 10 and an X-ray 11 dispersed by the second pattern 5b result in an X-ray intensity distribution 12 and an X-ray intensity distribution 13 with a linear form. The first and second pattern forms are characterized to be formed based on the intensities of the X-ray reflectance as a reference of the energy position and the X-ray reflectance of a target to be measured. If the plurality of patterns are incorporated in accordance with a formation process of the design rule, the relative positional displacement of the patterns is reduced, thus enabling to perform the detection with high accuracy.

In the diffraction grating 4 of FIG. 3, it is described that conventionally two patterns are formed, that is, the first pattern 5a and the second pattern 5b. However, the number of the patterns is not limited to two, and two or more patterns may be formed. The area ratio of the patterns is the same in FIG. 3. However, it is possible to attain preferable detection sensitivity, if the area ratio is determined, based on a certain level for optimally obtaining the X-ray reflectance or X-ray intensity to be measured.

Figure 9A:
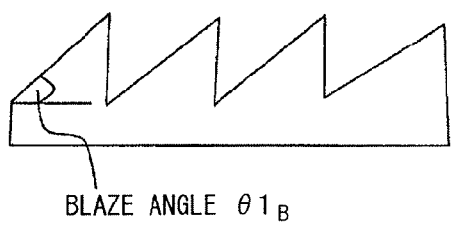
FIG. 9A is a diagram for explaining a pattern of spectroscopic elements of an X-ray analyzer as an embodiment of the present invention.
Figure 9B:
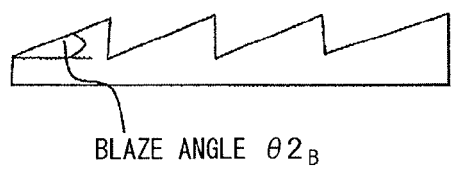
FIG. 9B is a diagram for explaining a pattern of spectroscopic elements of an X-ray analyzer as an embodiment of the present invention.

FIG. 9A and FIG. 9B illustrate an example of a cross sectional view of the first pattern 5a and the second pattern 5b in the diffraction grating 4 of FIG. 3. The first pattern of the diffraction grating illustrated in FIG. 9A and the second pattern illustrated in FIG. 9A are so-called sawtooth-formed groove type blazed diffraction grating pattern forms. For conventional sake, FIG. 9A and FIG. 9B illustrate flat type and regularly spaced pattern forms. However, in this embodiment, to reduce aberration in the diffraction grating, a concave formed and irregularly spaced diffraction grating pattern is used for the first and second patterns.

Figure 10:
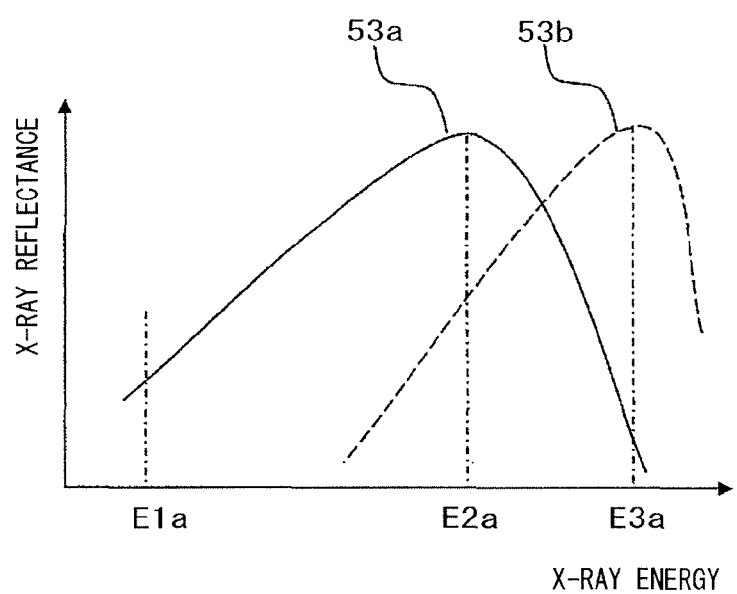
FIG. 10 is a diagram for explaining the energy dependence of the X-ray reflectance as an embodiment of the present invention.

FIG. 10 illustrates X-ray energy dependence of X-ray reflectance of a blazed type one. In FIG. 10, on the condition that inclination angles (so-called blaze angles) $\theta B$ are $\theta 1B$ (the first pattern 5a) and $\theta 2B$ (the second pattern 5b), the X-ray energy dependences of the X-ray reflectance are respectively a curve 53a and curve 53b. The blaze angle $\theta B$ is changed. That is, the blaze angle $\theta B$ of the first pattern 5a is $\theta 1B$, where the X-ray reflectance of the target to be evaluated for X-ray energy $E2a$ becomes highest. The blaze angle $\theta B$ of the second pattern 5b is $\theta 2B$, where the X-ray reflectance of energy $E3a$ as an X-ray energy reference is highest. Changing the blaze angle causes a change in the X-ray reflectance of the pattern of the blazed diffraction gratings.

Figure 11:
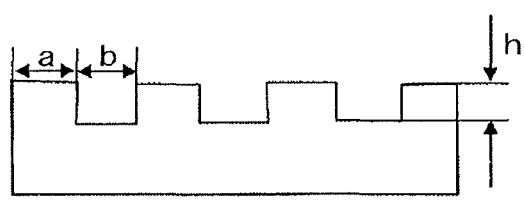
FIG. 11 is a diagram for explaining a pattern of spectroscopic elements of an X-ray analyzer as an embodiment of the present invention.

As illustrated in FIG. 11, another form may be used for the diffraction grating pattern. When a rectangular diffraction grating pattern is used, it is possible to change the X-ray reflectance by changing the height of the rectangular part, the depth of the grooves ("h" of FIG. 11), or the width ("a", "b" of FIG. 11) of the convex and concave parts. By changing the material to be used in the pattern or the material of a film to coat the pattern, it is possible to change the X-ray reflectance. Accordingly, those spectroscopic elements having the pattern for dispersing the X-ray can be applied to the present invention, regardless of the spectroscopic method or the kind of the diffraction grating.

Figure 12:
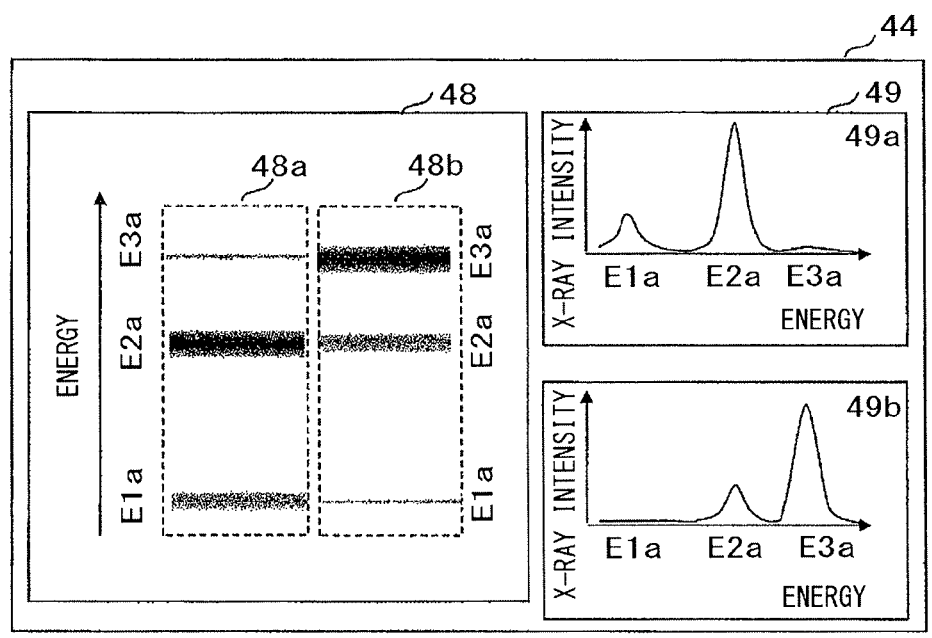
FIG. 12 is a diagram for explaining an operation unit of the electron beam analyzer as an embodiment of the present invention.

As illustrated in FIG. 12, the X-ray 3 entering the diffraction grating 4 is dispersed by the first pattern 5a and the second pattern 5b formed in the diffraction grating 4. X-ray images detected by the X-ray position detector 14 have image distributions of an X-ray image 48a and an X-ray image 48b. In the X-ray image 48a, the part of the X-ray energy $E2a$ of the target to be evaluated has high X-ray intensity. In the X-ray image 48b, the part of $E3a$ as an X-ray energy reference has high X-ray intensity.

In the X-ray image 48a and the X-ray image 48b, the X-ray spectrums can be displayed on the spectrum display unit 44 as an X-ray spectrum 49a and an X-ray spectrum 49b. For the X-ray spectrums, the X-ray energy is plotted on the horizontal axis, while the integrated value or the average value of the X-ray image intensities is plotted on the vertical axis.

Based on the X-ray image 48b or the X-ray spectrum 49b, the energy E2a of the spectrum of the target to be evaluated can accuracy be evaluated, using the spectrum as the reference energy E3a. In the X-ray image 48a or the X-ray spectrum 49a, the spectrum of the target, to be evaluated, of the energy E2a has sufficiently high intensity. Thus, in addition to the evaluation of the element concentration with high sensitivity, it is possible to perform evaluation reflected in the shape of the spectrum (such as evaluation of the electronic structure) with high accuracy.

According to this embodiment, using an analytical electron microscope having an X-ray device including a plurality of patterns of diffraction grating, it is possible to simultaneously detect an X-ray spectrum as an energy reference and an X-ray spectrum of the target to be evaluated, and to perform the detection with high spectrum intensity.

Conventionally, it is possible to correct the X-ray energy positional displacement due to the positional displacement of the installation/replacement of the diffraction grating. At the same time, the position adjustment of the diffraction grating can be simplified, though the reduction in the energy positional displacement has required quite a long time. Thus, it has become possible to detect a very small concentration of elements within a short period of time or to perform high accuracy evaluation with a high energy resolution.

(Embodiment 2)

In this embodiment, descriptions will now be made to an example, in which an X-ray analyzer has been installed in a scanning transmission electron microscope (STEM).

Figure 13:
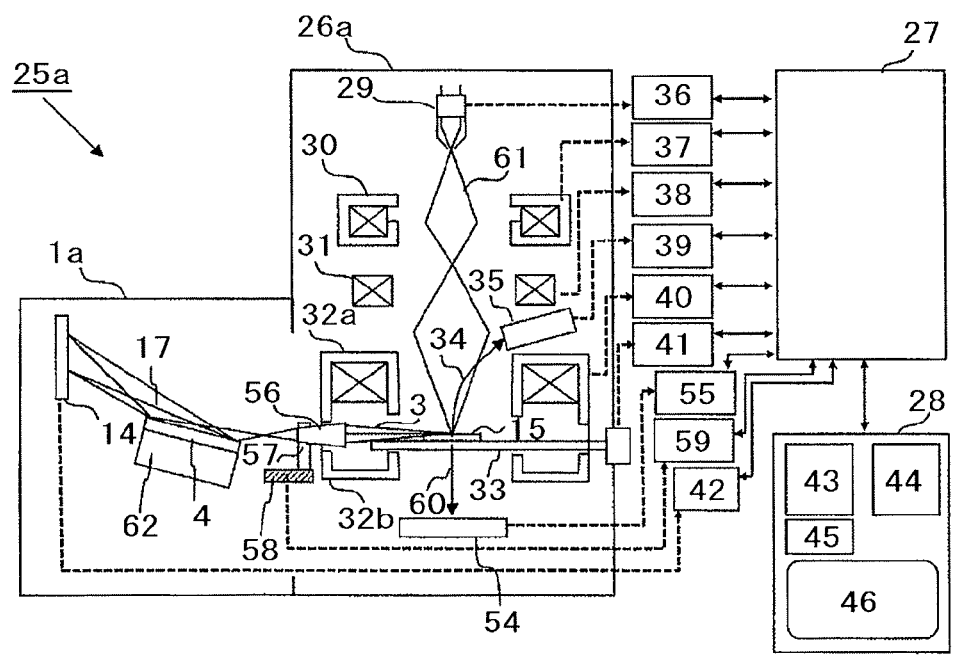
FIG. 13 is a block diagram of the electron beam analyzer as an embodiment of the present invention.

FIG. 13 illustrates that an X-ray analyzer 1 has been installed in a scanning transmission electron microscope 26a. The basic structure is the same as that of the X-ray analyzer 1 installed in the scanning electron microscope 26 illustrated in FIG. 5. However, an electron beam analyzer 25a has an X-ray condensing lens 56, an X lens holder 57, an X-ray lens driving unit 58, and an X-ray lens driving control unit 59. The lens 56 obtains an X-ray 3 generated by irradiating a sample 15 with an electron beam 61, at a high yield. The holder 57 holds the X-ray lens. The unit 58 drives the X-ray lens 56. The unit 59 controls the X-ray lens driving unit 58. In the embodiment 1, no descriptions have been made to the X-ray lens 56 for obtaining the X-ray at a high yield. However, the X-ray lens 56 may be installed in the scanning electron microscope 26.

n the case of the scanning transmission electron microscope 26a, in addition to a secondary electron detector 35 of the scanning electron microscope 26, a transmission scattering electron detector 54 is provided below the sample. This detector 59 irradiates the sample 15 with the electron beam 61 to detect electrons 60 transmitted through and scattered in the sample 15. The signal obtained by the transmission/scattering electron detector 54 is processed by a transmission scattering electron detection system circuit unit 55.

The transmission/scattering electron signal detected by the transmission/scattering electron detector 54 is synchronized with a primary electron beam 61 and output. As a result, a transmission/scattering electron image of the sample 15 can be displayed on the image display unit 43. In general, the intensity of scattered electrons is in proportion to an atomic number (Z) included in the sample, thus it is called as a Z contrast image.

As illustrated in FIG. 13, in the scanning transmission electron microscope 26a, an objective lens 32 is formed of an upper magnetic pole 32a and a lower magnetic pole 32b. The X-ray lens 56 introducing the X-ray is provided between the objective lens upper magnetic pole 32a and the lower magnetic pole 32b. Due to a space constraint between the objective lens upper magnetic pole 32a and the lower magnetic pole 32b, there may be also a constraint on increasing the diameter of the X-ray condensing lens 56. In this case, the X-ray condensing lens 56 is put closer to the sample 15 by the X-ray lens driving unit 58, thereby enabling to increase the yield of the X-ray.

In the scanning transmission electron microscope 26a, the primary electron beam probe diameter can be narrower than the scanning electron microscope 26. Thus, in the electron beam analyzer 25a in which the X-ray analyzer 1a is installed in the scanning transmission electron microscope 26a, an electron beam can be applied toward a very minute region. Therefore, it is possible to detect a very small concentration of elements and to perform the analysis with a high energy resolution, like the embodiment 1, with a higher spatial resolution.

Accordingly, the descriptions have been made to the inventions attained by the present inventors are not limited to the above-described embodiments, and various changes may be made without departing from the scope and spirit thereof.

LIST OF REFERENCE SIGNS 1, 1a: X-Ray Analyzer, 2: X-Ray Light Source, 3: X-Ray, 4: Diffraction Grating, 5a: First Pattern, 5b: Second Pattern, 6, 7, 10, 11, 17: Dispersed X-Ray, 8, 9, 12, 13: X-Ray Intensity Distribution With Linear Form, 14: Position Detector, 15: Sample, 16: Planer Shaped Diffraction Grating With Multilayer Film, 18: X-Ray Detector, 19: X-Ray Condensing Lens For Obtaining Parallel Light, 20: Curved Type Diffraction Grating, 21: Rowland Circle, 22, 23, 24, 53a, 53b: X-Ray Reflectance Curve, 25, 25a: Electron Beam Analyzer, 26: Scanning Electron Microscope, 26a: Scanning Transmission Electron Microscope, 27: Control System, 28: Operation Unit, 29: Electron Gun, 30: Condenser Lens, 31: Deflector, 32: Objective Lens, 33: Sample Stage, 34: Secondary Electron, 35: Secondary Electron Detector, 36: Electron Gun Control Unit, 37: Condenser Lens Control Unit, 38: Deflector Control Unit, 39: Objective Lens Control Unit, 40: Secondary Electron Detection System Circuit Unit, 41: Stage Control Unit, 42: X-Ray Detection System Circuit Control Unit, 43: Image Display Unit, 44: X-Ray Image and X-Ray Spectrum Display Unit, 45: Storage Unit, 46: Operation Screen, 47: Secondary Electron Image, 48: X-Ray Image, 49: X-Ray Spectrum, 50, 50a, 50b, 50c, X-Ray Intensity Distribution, 51a, 51b, 51c, X-Ray Spectrum, 52: Element Map Image, 54: Transmission Scattering Electron Detector, 55: Transmission Scattering Electron Detection System Circuit Unit, 56: X-Ray Condensing Lens, 57: X Lens Holder, 58: X-Ray Lens Driving Unit, 59: X-Ray Lens Driving Control Unit, 60: Transmission/Scattering Electron, 61: Primary Electron Beam, 62: Diffraction Grating Position/Rotation Adjustment Mechanism

The invention claimed is:

1. A spectroscopic element comprising:
a first pattern for dispersing an irradiated X-ray into a first spectrum having a first plurality of intensity distributions each having a linear form; and
a second pattern for generating a second spectrum different from the first pattern and having a second plurality of intensity distributions each having a linear form, for said irradiated X-ray, wherein said first and second patterns of said spectroscopic element are arranged side-by-side with respect to each other on said spectroscopic element in a direction of the linear form to cause said second plurality of intensity distributions to be disposed side-by-side in a direction orthogonal to said direction of the linear form with said first plurality of intensity distributions on an X-ray position detector in correspondence with said first and second patterns, wherein said first and second patterns of said spectroscopic element are further arranged to cause each said intensity distribution of said first plurality of intensity distributions to be disposed on the X-ray position detector collinearly head-to-tail in said direction of the linear form with a corresponding intensity distribution of said second plurality of intensity distributions, and wherein an area ratio of the first pattern to the second pattern is determined based on an X-ray, reflectance as an energy reference and an X-ray reflectance of a target to be evaluated.

2. The spectroscopic element according to claim 1, wherein
a shape of the first pattern is determined based on X-ray reflectance as an energy reference, and
a shape of the second pattern is determined based on X-ray reflectance of a target to be evaluated.

3. The spectroscopic element according to claim 1, wherein
a material of the first pattern or a material of a coating film is determined based on an X-ray reflectance as an energy reference, and
a material of the second pattern or a material of a coating film is determined based on an X-ray reflectance of a target to be evaluated.

4. The spectroscopic element according to claim 1, wherein
the first pattern and the second pattern are provided in accordance with a design rule which determines a relative positional displacement of said first and second patterns.

5. The spectroscopic element according to claim 1, wherein
the first pattern and the second pattern are provided on a same plane surface or a same curved surface.

6. The spectroscopic element according to claim 1, wherein
the first pattern and the second pattern are provided in an irradiated region of the X-ray.

7. A charged particle beam device comprising:
an irradiation optical system which applies a charged particle beam to a sample; and
an X-ray detection system which detects an X-ray generated from the sample, and wherein
the X-ray detection system has a spectroscopic element having
a first pattern for dispersing an irradiated X-ray into a first spectrum having a first plurality of intensity distributions each having a linear form; and
a second pattern for generating a second spectrum different from the first pattern and having a second plurality of intensity distributions each having a linear form, for said irradiated X-ray, wherein said first and second patterns of said spectroscopic element are arranged side-by-side with respect to each other on said spectroscopic element in a direction of the linear form to cause said second plurality of intensity distributions to be disposed side-by-side in a direction orthogonal to said direction of the linear form with said first plurality of intensity distributions on an X-ray position detector in correspondence with said first and second patterns, wherein said first and second patterns of said spectroscopic element are further arranged to cause each said intensity distribution of said first plurality of intensity distributions to be disposed on the X-ray position detector collinearly head-to-tail in said direction of the linear form with a corresponding intensity distribution of said second plurality of intensity distributions, and wherein an area ratio of the first pattern to the second pattern is determined based on an X-ray reflectance as an energy reference and an X-ray reflectance of a target to be evaluated.

8. The charged particle beam device according to claim 7, wherein
a shape of the first pattern is determined based on X-ray reflectance as an energy reference, and
a shape of the second pattern is determined based on X-ray reflectance of a target to be evaluated.

9. The charged particle beam device according to claim 7, wherein
the first pattern and the second pattern are provided in accordance with a design rule which determines a relative positional displacement of said first and second patterns.

10. The charged particle beam device according to claim 7, further comprising
an X-ray lens provided on an optical path of the sample and the spectroscopic element.

11. The charged particle beam device according to claim 10, further comprising
a control unit which moves the X-ray lens within a range of the optical path of the sample and the spectroscopic element.

* * * * *